US009053415B2

(12) United States Patent
Le Jeune (10) Patent No.: US 9,053,415 B2
(45) Date of Patent: Jun. 9, 2015

(54) METER FOR A DEVICE FOR DISPENSING A FLUID OR POWDER PRODUCT

(75) Inventor: Erwann Le Jeune, Saint Herblain (FR)

(73) Assignee: APTAR FRANCE SAS, Le Neubourg (FR)

( * ) Notice: Subject to any disclaimer, the term of this patent is extended or adjusted under 35 U.S.C. 154(b) by 831 days.

(21) Appl. No.: 13/266,668

(22) PCT Filed: Apr. 26, 2010

(86) PCT No.: PCT/FR2010/050787
§ 371 (c)(1),
(2), (4) Date: Dec. 14, 2011

(87) PCT Pub. No.: WO2010/125291
PCT Pub. Date: Nov. 4, 2010

(65) Prior Publication Data
US 2012/0090607 A1     Apr. 19, 2012

(30) Foreign Application Priority Data

Apr. 28, 2009   (FR) .................................... 09 52760

(51) Int. Cl.
*A62B 9/00*      (2006.01)
*G06M 1/04*      (2006.01)
*A61M 15/00*     (2006.01)

(52) U.S. Cl.
CPC ................ *G06M 1/04* (2013.01); *G06M 1/045* (2013.01); *A61M 15/0075* (2014.02)

(58) Field of Classification Search
CPC ............ G06M 1/045; A61M 15/0068; A61M 15/0065; A61M 15/007; A61M 15/0071; A61M 15/0073; A61M 15/0075; A61M 15/0076; A61M 15/0078; A61M 222/23

USPC ............ 128/200.24, 203.21, 205.23, 203.15; 116/284, 285, 298; 222/23
See application file for complete search history.

(56) References Cited

U.S. PATENT DOCUMENTS

| 2007/0210102 A1 | 9/2007 | Stradella et al. |
| 2009/0101150 A1 | 4/2009 | Stradella et al. |
| 2010/0083962 A1* | 4/2010 | Von Schuckmann .... 128/203.15 |

(Continued)

FOREIGN PATENT DOCUMENTS

| FR | 2 900 259 A1 | 10/2007 |
| WO | 2005/114563 A1 | 12/2005 |

OTHER PUBLICATIONS

International Preliminary Report on Patentability in International Application No. PCT/FR2010/050787 dated Apr. 26, 2010.

*Primary Examiner* — Lynne Anderson
*Assistant Examiner* — Bradley Philips
(74) *Attorney, Agent, or Firm* — Sughrue Mion, PLLC (57) ABSTRACT

A dose counter having a base body (460), with a rotary counter element assembled in the base body (460) on a pin (461) forming the axis of rotation. The rotary counter element co-operating with an actuator member (1430) adapted to cause the rotary counter element to turn each time the actuator member (1430) is actuated. The actuator member (1430) including a fastener (14301) for fastening to the base body (460) and arranged on a first side of the pin (461), and a substantially rigid support portion (1436) arranged on a second side of the pin (461). The support portion (1436) supporting an actuator element (1435) so that the actuator element (1435) is moved in translation. The support portion (1436) extended towards the pin (461) by a substantially-rectilinear flexible branch (1431) that supports a lug (14310) adapted to co-operate with the counter element on each actuation.

17 Claims, 5 Drawing Sheets

(56) References Cited

U.S. PATENT DOCUMENTS

2010/0212664 A1* 8/2010 Bishop ............... 128/200.23
2010/0229855 A1* 9/2010 Howgill .............. 128/200.23
2010/0263665 A1* 10/2010 Brown et al. ........ 128/203.12
2011/0253138 A1* 10/2011 Briant et al. ........ 128/203.12

* cited by examiner

METER FOR A DEVICE FOR DISPENSING A FLUID OR POWDER PRODUCT

CROSS REFERENCE TO RELATED APPLICATIONS

This application is a National Stage of International Application No. PCT/FR2010/050787 filed Apr. 26, 2010, claiming priority based on French Patent Application No. 09 52760 filed Apr. 28, 2009, the contents of all of which are incorporated herein by reference.

The present invention relates to a counter, and more particularly to a dose counter, for indicating to the user the number of doses that have been dispensed or that remain to be dispensed from a fluid or powder dispenser device.

The use of counters or of indicators is well known in the field of fluid dispensers, in particular in the field of pharmaceuticals. In particular, such counters or indicators are used with dispenser devices of the metered dose inhaler (MDI) type, in which a reservoir containing fluid and a propellant gas is movably mounted in a body, movement of said reservoir actuating a metering valve mounted on said reservoir, so as to dispense a dose of fluid. A first family of counters envisages fastening the counter on the bottom of the reservoir, projecting out from the body, and on which the user presses in order to dispense a dose. However, that type of counter presents the drawback of interfering with the actuation of the dispenser device, with it being necessary for the user to press on the counter in order to actuate the device. In the event of poorly controlled or partial actuation, problems of over- and/or under-counting and/or of incomplete or faulty dispensing may thus occur. A second family of counters comprises counters that are disposed inside the body, being fastened either to the body or to the movable reservoir in said body. In particular, that type of counter presents the drawback of a complex mounting, and requires substantial modifications to the various component parts of the dispenser device. The assembly problem occurs in particular when assembly is performed by the manufacturer of the pharmaceutical, as opposed to by the manufacturer of the dispenser device, with that requiring the manufacturer of the pharmaceutical to install complex assembly machines in its own factory. A third family of counters envisages arranging the counter on an outside face of the body, a projection of said counter passing through an opening in the body, so as to co-operate with the reservoir or a portion that is secured to said reservoir. That type of counter also generally requires substantial modification to the body in order to receive the counter. In addition, the presence of a counter on the outside main face of the body substantially modifies the external appearance of the device, in particular because of the thickness of said counter, and that may also have a negative effect on the handling of the device. In addition, the counters used on dispenser devices for dispensing fluids, in particular pharmaceuticals, need to comply with several constraints. Thus, in order to avoid any risk of under-counting, it is generally required that the counter is actuated at the very beginning of the actuation stroke of the valve or the pump, so as to avoid partial actuation, causing a partial or complete dose to be dispensed without any dose being counted by the counter. In this situation, a problem that occurs is that the actuation stroke is generally very short, and that the manufacturing tolerances of the device tend to reduce even further the distance available to perform the actuation in effective manner. The use of a complex mechanism is generally required in order to provide counting that is functional and safe. In general, assembling counters, in particular counters including a plurality of rotary elements that are interleaved in one another, is found to be complex and thus not only costly, but also a source of malfunctions. Documents FR 2 900 259 and WO 2005/114563 describe prior-art devices.

An object of the present invention is to provide a counter, more particularly a dose counter, for a fluid or powder dispenser device, that does not reproduce the above-mentioned drawbacks.

In particular, an object of the present invention is to provide such a counter that presents minimum thickness.

Another object of the present invention is to provide such a counter that can be pre-assembled prior to being delivered to the manufacturer of the pharmaceutical, said manufacturer thus needing only to perform a single step of mounting the counter on the body of the dispenser device, without any complex assembly of the component parts of said counter.

Another object of the present invention is to provide such a counter that guarantees actuation of the counter independently of the length of the actuation stroke of the pump or of the valve used in the device.

Another object of the present invention is to provide such a counter that is simpler and thus less costly to manufacture and to assemble, and that is more reliable in operation.

Another object of the present invention is to provide such a counter that optimizes the count display for the user.

The present invention thus provides a dose counter for counting the number of doses of fluid or powder that have been dispensed or that remain to be dispensed from a fluid dispenser device, said counter comprising a base body, with a rotary counter element being assembled in said base body on a pin forming the axis of rotation, said rotary counter element co-operating with an actuator member that is adapted to cause said rotary counter element to turn each time said actuator member is actuated, said counter being characterized in that said actuator member includes fastener means for fastening to the base body and being arranged on a first side of said pin, and a substantially rigid support portion that is arranged on a second side of said pin, said support portion supporting an actuator element so that, on each actuation, said actuator element is moved in translation, said support portion being connected to said fastener means via an elastically-deformable portion that surrounds said pin, said support portion being extended towards said pin by a substantially-rectilinear flexible branch that supports a lug that is adapted to co-operate with said counter element on each actuation.

Advantageously, said fastener means comprise a projection that penetrates into a hole of said base body.

Advantageously, said elastically-deformable portion includes two substantially-symmetrical sides that extend on each side of said pin, each side including a top deformable arc and a bottom deformable arc, said arcs being interconnected via a deformable baffle.

Advantageously, the deformation of the elastically-deformable portion during actuation causes the lug of the flexible branch to slope radially inwards.

Advantageously, said actuator member includes a guide second branch, substantially parallel to said flexible branch, for guiding the movement in translation of said actuator member.

Advantageously, said second branch co-operates with two projections of the base body by sliding in translation between said projections while the actuator member is being moved.

Advantageously, the free end of the flexible branch that supports the lug co-operates, in the non-actuated position, with an abutment of the base body.

Advantageously, said counter comprises: a first rotary counter element that is provided with a first peripheral edge portion including counter indices, such as one or more series of numbers from 0 to 9, in particular two series of numbers from 0 to 9, distributed over said periphery, and that is provided with a first set of teeth; and a second rotary counter element that is provided with a second peripheral edge portion including counter indices, such as numbers from 00 to 20, distributed over said periphery, and that is provided with a third set of teeth; the actuator member being movable between a first position and a second position, said flexible tab being adapted to co-operate with said first set of teeth of said first counter element, so as to cause said first counter element to turn when said actuator element is moved from its first position to its second position; said first counter element including at least one finger that is movable between a non-deformed position and a deformed position, which deformable finger is adapted, in its deformed position, to co-operate with said third set of teeth of said second counter element, so as to cause said second counter element to turn; said base body supporting said actuator member and said first and second counter elements, said base body including a cam that is adapted to deform said at least one deformable finger towards its deformed position.

Advantageously, said second peripheral edge portion of said second counter element is coplanar with, and radially outside, said first peripheral edge portion of said first counter element, said first and second counter elements not having a common axis, and being urged into contact with each other at a common display and/or counter zone.

Advantageously, said first counter element is provided with two deformable fingers that are diametrally opposite and that co-operate with a cam that is arranged radially on the outside, so that when a deformable finger co-operates with said cam, it is deformed radially inwards into its deformed position, so as to come into engagement with said third set of teeth of said second counter element.

Advantageously, said base body includes fastener means, such as snap-fastener tabs, for holding the actuator member and the first and second counter elements assembled on said base body, said counter possibly being pre-assembled so as to form a counter unit, said counter unit including fastener means for fastening to a body of a fluid dispenser device.

The present invention also provides a fluid or powder dispenser device comprising a reservoir, a dispenser member, such as a metering valve, that is mounted on said reservoir, and a body incorporating a dispenser orifice, said reservoir being movable in said body so as to dispense the fluid or powder, said dispenser device including a counter as described above.

Advantageously, said counter is fastened on a face of the body, said device being actuated by the user pressing axially on the reservoir, and said counter being actuated by said axial movement of said reservoir that co-operates with said actuator element of the actuator member.

These characteristics and advantages and others of the present invention appear more clearly from the following detailed description, given by way of non-limiting example, and with reference to the accompanying drawings, in which.

The counter of the present invention is applicable to any type of fluid or powder dispenser, but, more particularly, it applies to a dispenser device of the MDI type (not shown), in particular it is applied to its front main face. This type of device generally includes a body that is provided with a mouthpiece that defines a dispenser orifice. A reservoir is assembled in said body, said reservoir including a metering valve that is mounted on its opening. Inside said body, the metering valve co-operates with an expulsion channel that leads into the mouthpiece. When the user presses on the bottom of the reservoir, said reservoir slides axially inside the body, along the longitudinal axis of said body, causing the valve to be actuated and a dose of fluid to be expelled. The operation of such an MDI-type device is well known to the person skilled in the art, and is therefore not described more fully below. The counter may be interposed between the front main face of said body and a covering member that includes a window, and that may serve to fasten the counter on the body. Naturally, this embodiment is only an example, and, by way of example, the counter could be fastened directly to the body, independently of the presence of a covering member. The counter includes an actuator element 1435 (visible in FIGS. 1, 2, 4b, 6a, 6b, and 9) that projects out from said counter, and that is adapted to penetrate inside the body through an opening that is provided for this purpose, so as to co-operate with the reservoir or with a portion that is secured to said reservoir. In this way, each time the dispenser device is actuated, the axial movement of the reservoir in the body causes the actuator element to move.

The counter of the invention includes an actuator member 1430. The actuator member 1430 that includes the actuator element 1435, is for transforming an axial movement, along the longitudinal axis of the body, of a portion of the dispenser device, generally the reservoir, into a turning movement of the counter element 410 with which it co-operates.

In an advantageous variant embodiment the counter is arranged substantially vertically and on a face of the body of the dispenser device when it is in its normal working position, and the actuator member 1430 thus transforms an axial movement of the reservoir, along the longitudinal axis of the body, into a turning movement of the counter element 410 about its axis of rotation. In this embodiment, the axis of rotation of the counter element 410 is substantially perpendicular to the longitudinal axis of the body. Advantageously, the actuation cycle of the counter may start at the very beginning of the stroke of the reservoir, such that the counter is actuated before any fluid is dispensed.

As shown in FIGS. 1 to 5, the counter preferably includes a base body 460 to which a lid (not shown) may be associated. Said base body forms the lug 461 that forms the pivot pin of the counter element 410, and includes an opening 465 through which the actuator element 1435 is able to pass. The lid may include a viewing window enabling the user to see the display zone that is formed on the counter element 410. The base body 460 may include fastener means 467, such as snap-fastener tabs, that are adapted to fasten the outer edge of the counter element 410, without however limiting its capacity to turn about its pin. The counter element 410 holds the actuator member 1430 in the base body 460. Thus, said counter may advantageously be pre-assembled so as to form a counter unit, said counter unit possibly including fastener means for fastening to the body of the fluid dispenser device.

In the invention, said actuator member 1430 is assembled in said base body 460. Said actuator member 1430 includes fastener means 14301 for fastening to the body 460, e.g. a projection 14301 that penetrates into a hole 466 of the body 460. The projection 14301 is arranged on a first side of the pin 461 forming the axis of rotation A of the counter element 410, in particular above said pin in the position shown in FIG. 5. Said actuator member 1430 also includes a substantially rigid support portion 1436 that is arranged on a second side of said pin 461, in particular below said pin in FIG. 5. Said support portion 1436 supports the actuator element 1435 that co-operates with the reservoir or bottle of the device on which the counter is assembled, so that, on each actuation, said actuator element 1435 is moved in translation along the longitudinal axis of the body. Said support portion 1436 is connected to said projection 14301 via an elastically-deformable portion 14341, 14342, 14343 that surrounds said pin 461 and that forms a spring. The elastically-deformable portion may include two sides, advantageously approximately symmetrical, that connect said projection 14301 to said support portion 1436, respectively on each lateral side of said pin 461, in the position in FIG. 5. Each side may include a top deformable arc 14341 that is connected to said projection 14301, and a bottom deformable arc 14343 that is connected to said support portion 1436. The arcs may be connected via a deformable baffle 14342. Said support portion 1436 is extended towards said pin 461 by a substantially-rectilinear flexible branch 1431 that supports a lug 14310 that is adapted to co-operate with said counter element 410 on each actuation. The actuator member 1430 thus surrounds the counter element 410, and in particular a first set of teeth 411 thereof. This embodiment provides actuation that is particularly reliable, by accurately defining the vertical and horizontal positions of the actuator member 1430, and by providing optimum meshing of the lug 14310 in the first set of teeth 411.

Figure 6A:
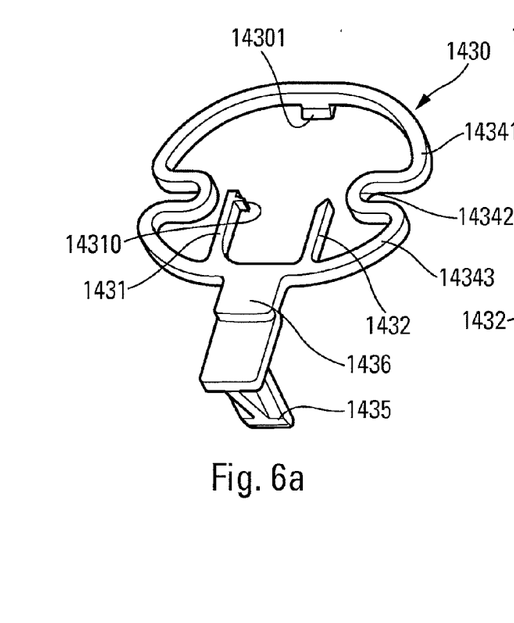
FIGS. 6a and 6b are perspective front and rear views of the FIG. 5 actuator member.
Figure 6B:
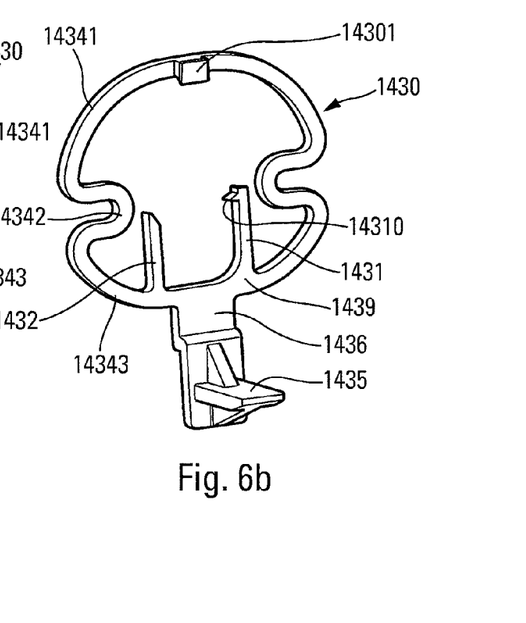

Thus, the bottom portion of the actuator member 1430 has a downward movement that is generated by the reservoir bearing on the actuator element 1435. The downward vertical movement along the longitudinal axis of the body drives the lug 14310, carried by the branch 1431 that pulls of the lug. The lug 14310 thus turns the counter element 410 about its axis of rotation by meshing on the first set of teeth 411. The terms "vertical" and "horizontal" used in the present description refer to the positions in FIGS. 2 and 6, i.e. with a longitudinal axis of the body that is substantially vertical, and an axis of rotation of the counter element that is substantially horizontal.

The shapes of the actuator member 1430 and the material that constitutes it ensures that during the downward vertical movement, the lug 14310 is driven in an equivalent vertical-component movement.

The branch 1431 is flexible so as to enable the lug 14310 to escape behind the following tooth of the first set of teeth 411 while the actuator member 1430 is rising, so as to return to its non-actuated initial position.

The flexibility of the branch 1431 is adjusted by determining its width, so as to impart thereto stiffness that is sufficient for the lug 14310 to turn the counter element 410 by the amount necessary to count one unit while the actuator member is moving downwards.

The projection 14301 makes it possible to position the actuator member 1430 vertically in the body 460. In combination with the top end of the branch 1431 that co-operates with an abutment 462 of the body 460, the projection 14301 also ensures that the lug 14310 is positioned at the correct height relative to the first set of teeth 411. The counter element 410 is positioned in the body 460 by interfitting on the pin 461. The vertical positioning of the lug 14310 relative to the first set of teeth 411 thus also defines the start of the drive stroke for driving the counter element 410 by the lug 14310.

A vertical-guide second branch 1432, advantageously approximately parallel to the branch 1431, is guided in vertical translation in the body 460, e.g. by co-operating with one or more appropriate projections 4650 and 4651. In the embodiment shown in FIG. 5, the branch 1432 slides between two projections 4650 and 4651 of the body 460. The second branch 1432 provides the horizontal positioning of the actuator member 1430, in particular while it is moving. It also defines the initial horizontal position of the lug 14310 relative to the first set of teeth 411.

While the actuator member 1430 is moving downwards, the projection 14301 remains stationary in the body 460, the arcs 14341 and 14343 deform, as do the baffles 14342. The deformations remain in proportions that make it possible to avoid any plastic deformation, and in this way ensures that the actuator member 1430 returns to its initial shape and to its initial position when the pressure on the actuator element 1435 is relaxed.

The dimensions of the arcs 14341, 14343 and of the baffles 14342 are also adjusted so as to provide sufficient capacity to return to their initial shapes and positions while taking into account the stresses braking such return as generated by the flexing of the branch 1431 during the passage of the lug 14310 behind the following tooth of the first set of teeth 411.

The shape of the connection zone 1439 between the support portion 1436 and the flexible branch 1431 is designed so as to ensure that while the actuator member 1430 is being pulled vertically downwards by pressing on the actuator element 1435, the deformation of the arcs 14341 causes the branch 1431 to slope towards the pin 461. The sloping of the branch 1431 helps the lug 14310 to mesh properly with the first set of teeth 411, and to avoid becoming unmeshed prematurely while the actuator member 1430 is moving downwards.

Since the actuation of the valve generally requires a greater stroke, and thus a greater axial movement of the reservoir along the longitudinal axis of the body, the deformable portion 14341, 14342, 14343 of the actuator member 1430 makes it possible to continue the axial movement of the reservoir to its full stroke. In addition, the system makes it possible to actuate the counter before beginning to dispense the fluid.

The invention applies to counters that include only a single rotary counter element 410. However, the following description relates to the preferred embodiment shown in the drawings, in which there are two rotary counter elements, namely a first rotary counter element 410, shown in detail in FIGS. 8a and 8b, and a second rotary counter element 420, shown in detail in FIGS. 7a and 7b.

Figure 4A:
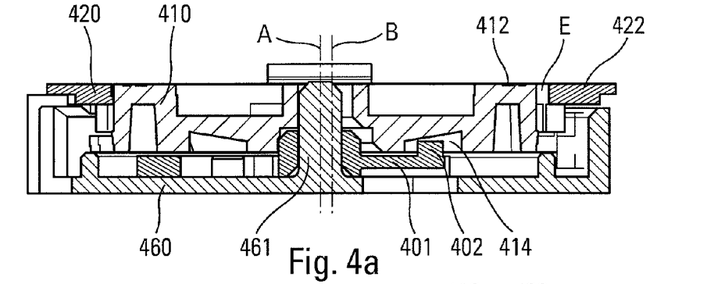
FIG. 4a is a diagrammatic cross-section view of the FIG. 3 counter.

When there are two rotary elements 410, 420, said rotary elements may turn about a common axis of rotation that is substantially perpendicular to the longitudinal axis of the body. In a variant, the two rotary elements 410, 420 may turn about two axes of rotation A and B that are parallel to, but slightly offset from, each other, as shown in FIG. 4a.

Figure 1:
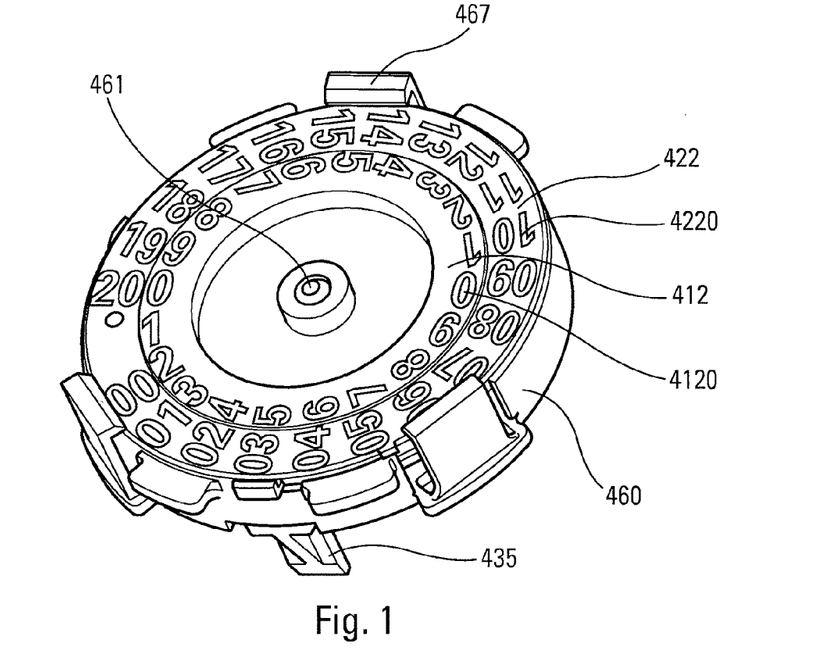
FIG. 1 is a diagrammatic perspective front view of a counter, in an advantageous embodiment of the present invention.
Figure 2:
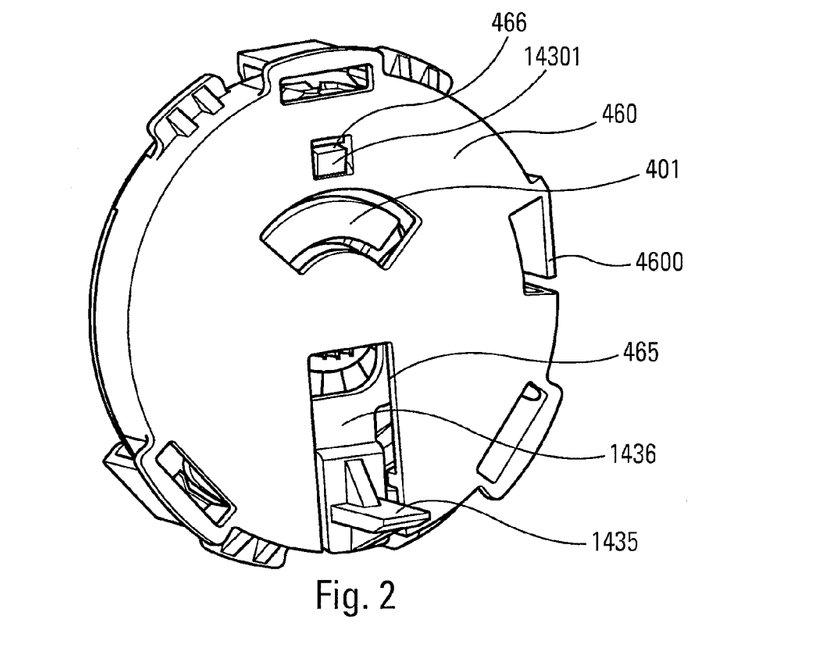
FIG. 2 is a view similar to the view in FIG. 1, but as seen from the rear.
Figure 3:
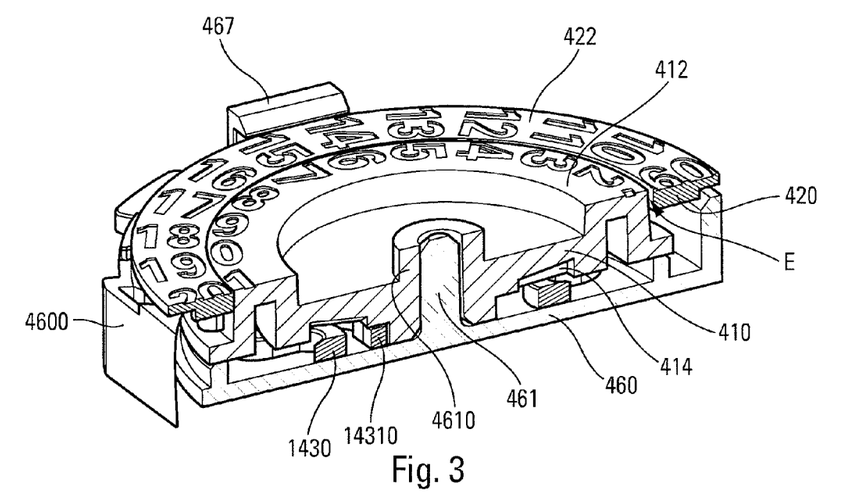
FIG. 3 is a diagrammatic and partially cut-away perspective view of two rotary counter elements, in an advantageous embodiment of the invention.

In the preferred embodiment shown in the drawings, the first rotary counter element 410 forms the units wheel, and the second rotary counter element 420 forms the tens wheel, said first and second counter elements co-operating with each other to define a common display and/or counter zone that is visible in a viewing window (not shown). The counter zone may display the number of doses of fluid that have been dispensed or that remain to be dispensed from said reservoir. In FIG. 1, the common display and/or counter zone is formed at number 200. Preferably, the dose number is displayed horizontally in the display zone when the dispenser device is in its normal working position in which the body is substantially vertical with the mouthpiece arranged at the bottom. Said first counter element 410 co-operates with the actuator member 1430 that is adapted to cause said first counter element 410 to turn each time said actuator member is actuated, as described above. Interconnection means are adapted to cause said second counter element 420 to turn on every tenth actuation of said actuator member 1430, and thus on every tenth turn of said first counter element 410.

Advantageously, both counter elements are assembled in rotary manner around two axes of rotation A and B that are offset from each other. Thus, as visible in FIGS. 3 and 4a, the first counter element 410 may be assembled on a pin 461 of the body 460, e.g. via a sleeve 4610, said pin forming the axis of rotation A of the first counter element 410. The second counter element 420 is assembled on the first counter element 410. Advantageously, such assembly is achieved by mounting a second peripheral edge portion 422 of the second counter element 420 around a first peripheral edge portion 412 of the first counter element 410. Advantageously, the inside diameter of the second peripheral edge portion 422 is greater than the outside diameter of the first peripheral edge portion 412. The body 460 includes radial bias means, such as a resilient tab or spring blade 4600, for applying radial bias relative to the axis of rotation, said means pushing the second counter element 420 radially into contact with the first counter element 410 at a contact point that is situated at the common display and/or counter zone. Thus, with different diameters, and in contact only at one point on their peripheries, the two counter elements 410 and 420 do not have a common axis, and they turn about axes of rotation A and B that are parallel to, and offset from, each other. In particular, this is shown by the offset E that is visible in FIGS. 3 and 4a, and that is at its maximum at the point that is diametrically opposite the contact point. The offset E that should be as small as possible, is at least 0.1 mm, but advantageously it should be at least 0.2 mm, in particular so as to take into account manufacturing tolerances, possible ovalizing phenomena of the counter elements, and/or expansion offsets between the two counter elements. This embodiment makes it possible to guarantee an optimum display and/or counter zone in which the two counter elements 410, 420 are in contact, without any space between the numbers, and with the numbers in perfect alignment. This embodiment also makes it possible to optimize friction between the two counter elements. In particular, such friction may not only be reduced, but it may be possible to manage it more accurately. The contact point may also perform a non-return function for the second counter element 420.

As shown in FIGS. 1 to 5, the base body forms the pin 461 forming the axis of rotation A of the first counter element 410. The viewing window enables the user to see the display zone that is formed jointly by said first and second counter elements 410, 420. The fastener means 467, such as snap-fastener tabs, are adapted to fasten the outer edge of the second counter element 420, without however limiting its capacity to turn about its axis B. The second counter element 420 retains the first counter element 410 that in turn retains the actuator member 1430 in the base body 460. Thus, said counter may advantageously be pre-assembled so as to form a counter unit, said counter unit possibly including fastener means for fastening to the body of the fluid dispenser device.

Figure 8A:
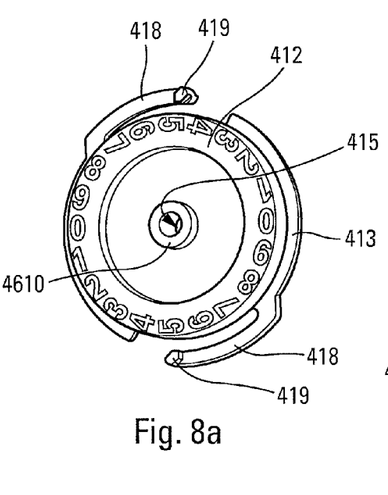
FIGS. 8a and 8b are diagrammatic front and rear views respectively of the first rotary counter element, in an advantageous variant embodiment.
Figure 8B:
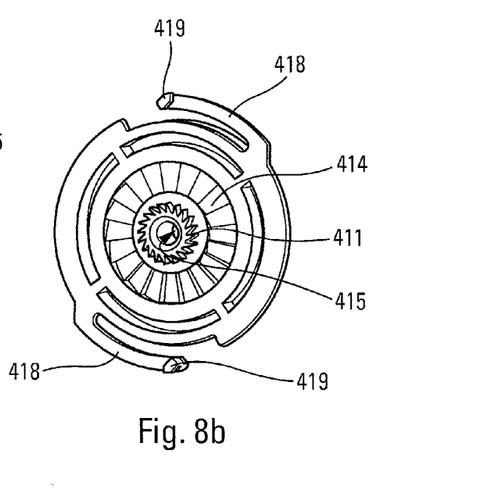
Figure 9:
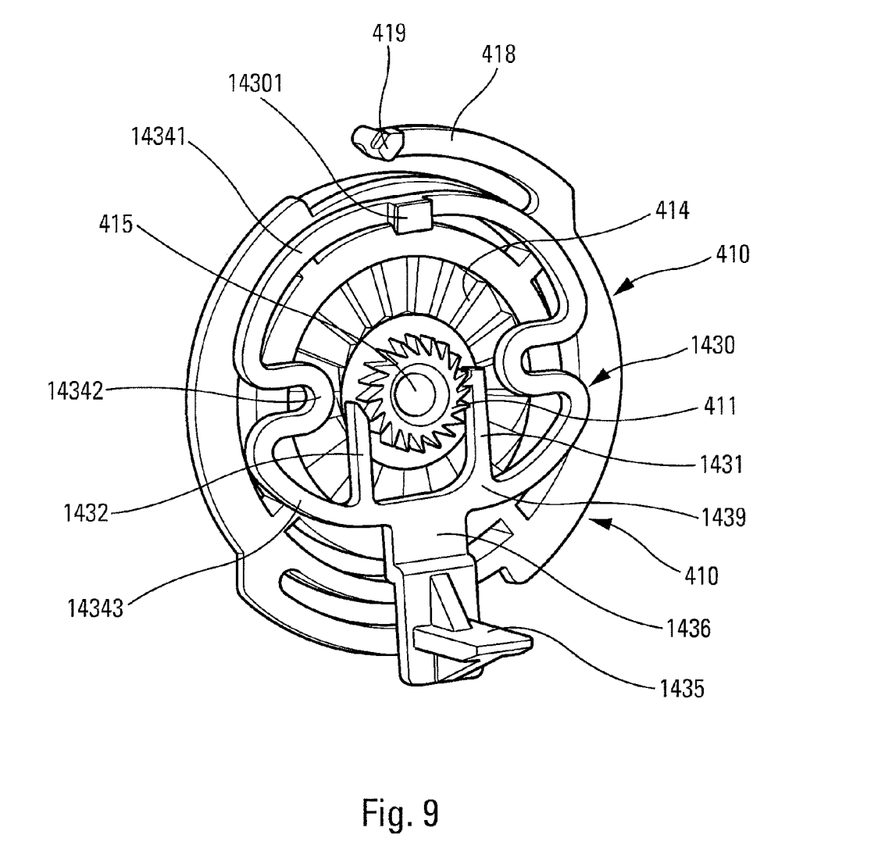
FIG. 9 is a diagrammatic perspective view of the actuator element co-operating with the rotary counter element.

As shown in FIGS. 8a and 8b, said first counter element 410 may include a first peripheral set of teeth 411, which set, on each actuation, co-operates with a flexible actuator tab 1431 of the actuator member 1430. The first counter element may also include a second set of peripheral teeth 414. Advantageously, said first counter element 410 is substantially disk shaped, being provided with a central through opening 415 that is defined by the sleeve 4610 and that is adapted to be engaged around the pin 461 forming its axis of rotation A. The top face of said disk includes a first peripheral edge portion 412 that receives counter indices 4120, such as one or more series of numbers from 0 to 9. The example shown in FIGS. 1 and 8a shows two series of numbers from 0 to 9, distributed over said periphery. The bottom face of said disk includes said first and second peripheral sets of teeth 411, 414, as visible in FIG. 8b. Preferably, the teeth of the second set of teeth 414 are oriented axially relative to the axis of rotation so as to co-operate with non-return means 401, 402 that are provided in the body 460. As visible in FIG. 5, the non-return means may comprise a deformable tab 401 that supports a non-return tooth 402 for co-operating with the second set of teeth 414. As visible in FIG. 8, the top face of said first counter element 410 may include a central plane portion that surrounds the central opening 415 and that is extended radially outwards, relative to the axis of rotation, by said first peripheral edge portion 412 that is raised axially relative to said central portion. The first peripheral edge portion 412 may be extended radially outwards relative to the axis of rotation by an outer plane portion 413 that does not extend over the entire periphery, but that is interrupted by at least one, preferably two, flexible tabs 418 each of which includes a respective lug 419 at its end. The flexible tabs 418 extend in peripheral manner, and the lug 419 may extend perpendicularly to its respective tab 418, as visible in FIGS. 8a and 8b. This embodiment makes it possible to superpose the second counter element 420 on the first counter element 410 with an overall thickness that is small.

Figure 7A:
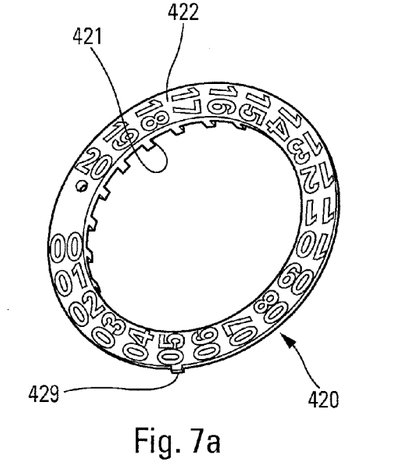
FIGS. 7a and 7b are diagrammatic front and rear views respectively of the second rotary counter element, in an advantageous variant embodiment.
Figure 7B:
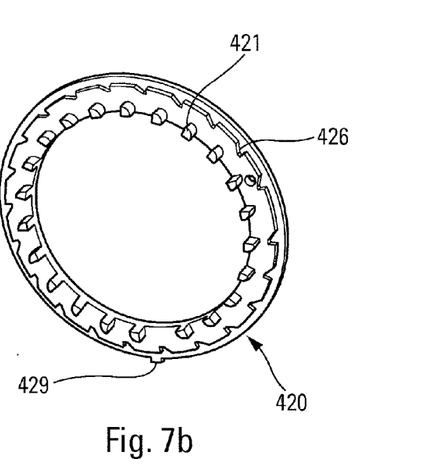

As shown in FIGS. 7a and 7b, said second counter element 420 may include a third peripheral set of teeth 421, which set is adapted, on every tenth actuation of the actuator member 1430, to co-operate with a lug 419 of said first counter element 410. Advantageously, said second counter element 420 is substantially ring shaped, adapted to be arranged on said outer portion of said first counter element 410. The top face of said ring includes a second peripheral edge portion 422 that is radially on the outside relative to the axis of rotation and that receives counter indices 4220, such as the numbers from 00 to 20, distributed over said periphery. In this example, the counter is thus capable of counting 200 doses. The bottom face of said ring includes said third peripheral set of teeth 421, arranged radially on the inside relative to the axis of rotation, and extending axially downwards, and a fourth peripheral set of teeth 426, arranged radially outside said bottom face relative to the axis of rotation. The fourth set of teeth 426 is adapted to co-operate with at least one projection that is provided on the base body 460 so as to act as non-return means. Advantageously, after assembling the first and second counter elements 410, 420, said second peripheral edge portion 422 of said second counter element 420 is arranged radially on the outside and substantially in contact with said first peripheral edge portion 412 of said first counter element 410, at the counter or display zone. The top surfaces of said first and second peripheral edge portions 412, 422 are substantially in alignment and coplanar at the display zone that is visible through the viewing window.

The first counter element 410 includes at least one deformable finger 418, preferably two diametrally-opposite fingers, the deformable finger(s) being adapted, on every tenth actuation, to co-operate with a cam 4605 that is secured to the base body 460. A plurality of cams may optionally be provided. In the embodiment shown in FIG. 5, the cam 4605 is at about 90° from the resilient blade 4600 that urges the two counter elements 410, 420 into contact. In a variant, the cam 4605 could be made in the proximity of, or even at the same location as, said resilient blade or tab 4609. As a result, the interconnection means would mesh at the location in which the offset E between the two counter elements was at its minimum, thereby making it possible to provide a greater offset between the two counter elements, without any risk of the interconnection means malfunctioning. The third set of teeth 421 of the second counter element 420 is for co-operating with the lug 419 of a deformable finger 418 of the first counter element each time said deformable finger is moved towards its deformed position by said cam 4605. More clearly, the cam provided in said base body is adapted to deform a deformable finger 418 resiliently and radially inwards relative to the axis of rotation, each time the lug 419 of said deformable finger 418 co-operates with said cam. When the finger 418 is not deformed, said lug 419 does not co-operate with said third set of teeth 421.

In the embodiment shown in the drawings, the first counter element 410 includes two diametrally-opposite fingers 418, and two series of numbers from 0 to 9, distributed over the periphery. On every tenth actuation, one of the two deformable fingers 418 co-operates with said cam, preferably provided radially on the outside relative to the axis of rotation and relative to said fingers, so as to deform them inwards and thus enable said lug 419 to co-operate with the third set of teeth 421 of the second counter element 420. The second counter element 420 is thus also turned. The fourth set of teeth 426 of the second counter element 420 is for co-operating with non-return means, e.g. a projection that may be secured to the base body 460. It should be noted that the non-return means could equally well co-operate with the third set of teeth, in which situation the second counter element 420 could include a single set of teeth only.

Figure 4B:
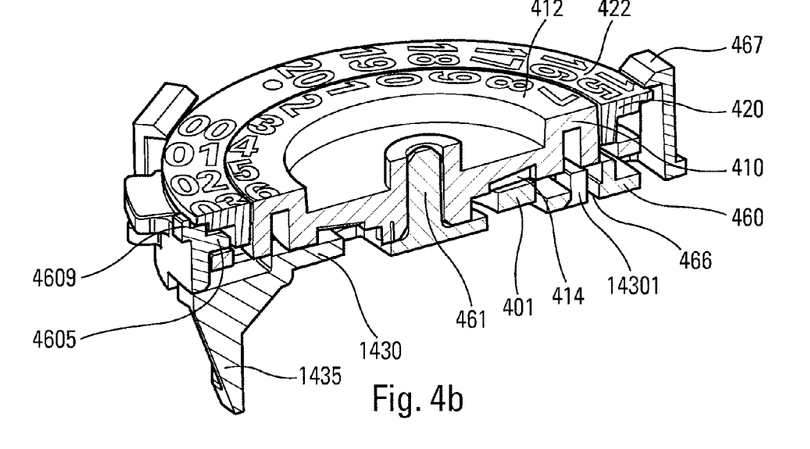
FIG. 4b is a view similar to the view in FIG. 3, partially cut-away in another section plane.
Figure 5:
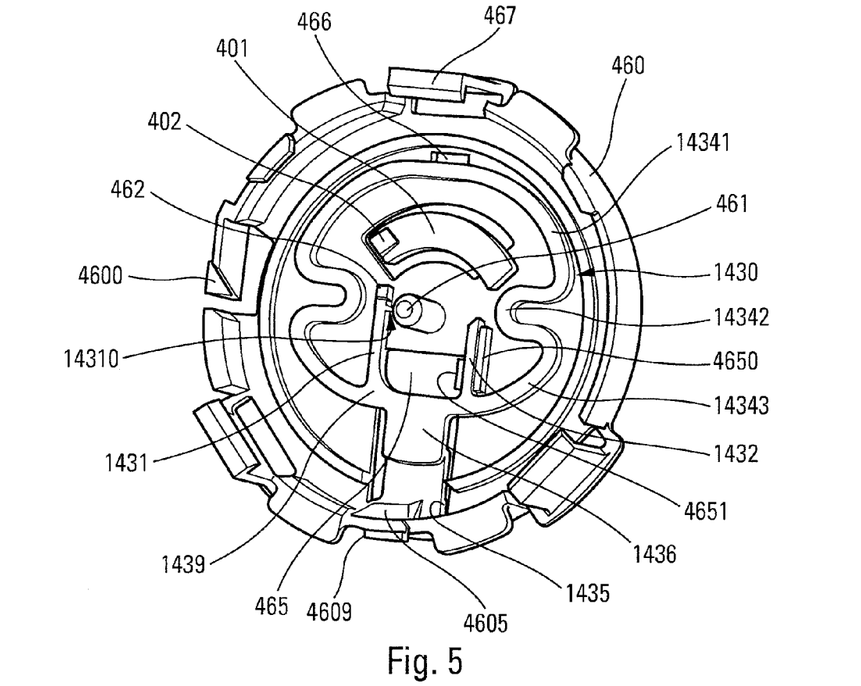
FIG. 5 is a diagrammatic perspective view of the actuator member of the counter, in an advantageous embodiment, shown assembled in the base body.

Advantageously, the second counter element 420 may include a blocking tooth 429 that projects radially outwards relative to the axis of rotation, and that is adapted to co-operate with an appropriate shoulder 4609 of the body 460, visible in FIG. 4b. Thus, for a counter that counts down, e.g. from 200 to 000, when the numbers 00 appear in the display zone, the second counter element is prevented from turning by the blocking tooth 429 co-operating with the shoulder 4609. When the first counter element 410 arrives in turn with a 0 in the display zone, it too is prevented from turning by a lug 419 co-operating with the blocked set of teeth 421 of the second counter element.

An advantage of the counter of the present invention is that it makes a large display possible, without increasing the bulkiness of the counter. In particular, the embodiment shown makes it possible for a 200-dose counter to display numbers (firstly units, secondly tens) having a height that is greater than 2 mm, preferably about 2.5 mm, and a width that is greater than 1.5 mm, preferably about 2 mm. This represents an increase in the physical size of the numbers of up to 50% relative to existing counters.

In the embodiment shown, the indicator is adapted to indicate the number of doses that remain to be dispensed, such that the number displayed decreases on each actuation. Naturally, the inverse is also possible, namely a counter that counts the number of doses that have been dispensed.

As a result of its components and of the arrangement of said components relative to one another, the counter of the invention thus makes it possible to make a counter that may be pre-assembled so as to form a counter unit, and that presents, in its pre-assembled state, a very small thickness, typically less than or equal to 7 mm, advantageously less than 6 mm, and possibly even less than 5 mm.

Various modifications may also be envisaged by a person skilled in the art, without going beyond the ambit of the present invention, as defined by the accompanying claims.

The invention claimed is:

1. A dose counter for counting the number of doses of fluid or powder that have been dispensed or that remain to be dispensed from a fluid dispenser device, said counter comprising a base body, with a rotary counter element being assembled in said base body on a pin forming the axis of rotation, said rotary counter element co-operating with an actuator member that is adapted to cause said rotary counter element to turn each time said actuator member is actuated, said actuator member includes fastener means for fastening to the base body and being arranged on a first side of said pin, and a substantially rigid support portion that is arranged on a second side of said pin, said support portion supporting an actuator element so that, on each actuation, said actuator element is moved in translation, said support portion being connected to said fastener means via an elastically-deformable portion that surrounds said pin, said support portion being extended towards said pin by a substantially-rectilinear flexible branch that supports a lug that is adapted to co-operate with said counter element on each actuation;

wherein the rotary counter element is a first rotary counter element that is provided with a first peripheral edge portion including counter indices distributed over said periphery, and that is provided with a first set of teeth; and the dose counter comprising a second rotary counter element that is provided with a second peripheral edge portion including counter indices distributed over said periphery, and that is provided with a third set of teeth;

wherein the actuator member is movable between a first position and a second position, said flexible tab adapted to co-operate with said first set of teeth of said first counter element, so as to cause said first counter element to turn when said actuator element is moved from its first position to its second position;

said first counter element including at least one finger that is movable between a non-deformed position and a deformed position, which deformable finger is adapted, in its deformed position, to co-operate with said third set of teeth of said second counter element, so as to cause said second counter element to turn;

said base body supporting said actuator member and said first and second counter elements, said base body including a cam that is adapted to deform said at least one deformable finger towards its deformed position.

2. The counter according to claim 1, wherein said fastener means comprise a projection that penetrates into a hole of said base body.

3. The counter according to claim 1, wherein said elastically-deformable portion includes two substantially-symmetrical sides that extend on each side of said pin, each side including a top deformable arc and a bottom deformable arc, said arcs being interconnected via a deformable baffle.

4. The counter according to claim 1, wherein the deformation of the elastically-deformable portion during actuation causes the lug of the flexible branch to slope radially inwards.

5. The counter according to claim 1, wherein said actuator member includes a guide second branch, substantially parallel to said flexible branch, for guiding the movement in translation of said actuator member.

6. The counter according to claim 5, wherein said second branch co-operates with two projections of the base body by sliding in translation between said projections while the actuator member (1430) is being moved.

7. The counter according to claim 1, wherein the free end of the flexible branch that supports the lug co-operates, in the non-actuated position, with an abutment of the base body.

8. The counter according to claim 1, wherein said second peripheral edge portion of said second counter element is coplanar with, and radially outside, said first peripheral edge portion of said first counter element, said first and second counter elements not having a common axis, and being urged into contact with each other at a common display and/or counter zone.

9. The counter according to claim 1, wherein said first counter element is provided with two deformable fingers that are diametrically opposite and that co-operate with a cam that is arranged radially on the outside, so that when a deformable finger co-operates with said cam, it is deformed radially inwards into its deformed position, so as to come into engagement with said third set of teeth of said second counter element.

10. The counter according to claim 1, wherein said base body includes fastener means for holding the actuator member and the first and second counter elements assembled on said base body, said counter possibly being pre-assembled so as to form a counter unit, said counter unit including fastener means for fastening to a body of a fluid dispenser device.

11. A fluid or powder dispenser device comprising a reservoir, a dispenser member that is mounted on said reservoir, and a body incorporating a dispenser orifice, said reservoir being movable in said body so as to dispense the fluid or powder, said dispenser device comprising the counter according to claim 1.

12. The device according to claim 11, wherein said counter is fastened on a face of the body, said device being actuated by the user pressing axially on the reservoir, and said counter being actuated by said axial movement of said reservoir that co-operates with said actuator element of the actuator member.

13. The counter according to claim 1, wherein the counter indices of the first rotary counter element are one or more series of numbers from 0 to 9.

14. The counter according to claim 1, wherein the counter indices of the first rotary counter element are two series of numbers from 0 to 9.

15. The counter according to claim 13, wherein the counter indices of the second rotary counter element are numbers from 00 to 20.

16. The counter according to claim 10, wherein the base body fastener means are snap-fastener tabs.

17. The fluid or powder dispenser device according to claim 11, wherein the dispenser member is a metering valve.

* * * * *